United States Patent [19]
Rosofsky et al.

[11] Patent Number: 5,472,665
[45] Date of Patent: Dec. 5, 1995

[54] PROCESS FOR TREATING COMPRESSED CELLULOSE AND APPLICATIONS THEREOF

[76] Inventors: Paul M. Rosofsky, 83 Sussex Dr., Willingboro, N.J. 08046; Seymour Gilbert, 76 Ross Hall Blvd. North, Piscataway, N.J. 08854

[21] Appl. No.: 7,350

[22] Filed: Jan. 21, 1993

[51] Int. Cl.[6] .......................... A61L 2/06; D06M 13/184; D06P 5/02
[52] U.S. Cl. .................... 422/27; 8/120; 8/125; 8/490
[58] Field of Search .............. 264/187; 134/27, 134/28, 29, 30; 8/107, 125, 127, 490, 518, 120, 116.1; 422/27, 28

[56] References Cited

U.S. PATENT DOCUMENTS

| | | | |
|---|---|---|---|
| D. 270,972 | 10/1983 | Rosofsky | D4/25 |
| 3,328,178 | 6/1967 | Alderton | 422/28 |
| 3,332,833 | 7/1967 | Guthrie | 8/125 X |
| 3,634,183 | 5/1970 | Viola et al. | 428/215 |
| 4,076,500 | 2/1978 | Rearick | 8/125 X |
| 4,165,743 | 8/1979 | Denning | 264/191 X |
| 4,312,634 | 1/1982 | Katz | 8/125 X |
| 4,486,109 | 12/1984 | Rosofsky | 401/24 |
| 4,506,988 | 4/1985 | Reed | 366/203 |
| 4,543,679 | 10/1985 | Rosofsky et al. | 15/110 |
| 4,608,968 | 9/1986 | Rosofsky | 128/62 |
| 4,817,333 | 4/1989 | Szepessy et al. | 422/28 X |

OTHER PUBLICATIONS

Block, Seymour S. *Disinfection, Sterilization, and Preservation*, 1983, pp. 1 and 14.

*Primary Examiner*—Robert J. Warden
*Assistant Examiner*—E. Leigh Dawson
*Attorney, Agent, or Firm*—Duane, Morris and Heckscher

[57] ABSTRACT

A method for removing impurities and potentially toxic substances from cellulose is disclosed. The method comprises the following steps: (a) immersing cellulose containing organic extractables in one or more acid baths so as to remove traces of organic extractables; (b) immersing the cellulose in a water bath; (c) immersing the compressed cellulose in an alkaline bath; and (d) sterilizing the treated cellulose using pressurized steam.

7 Claims, 7 Drawing Sheets

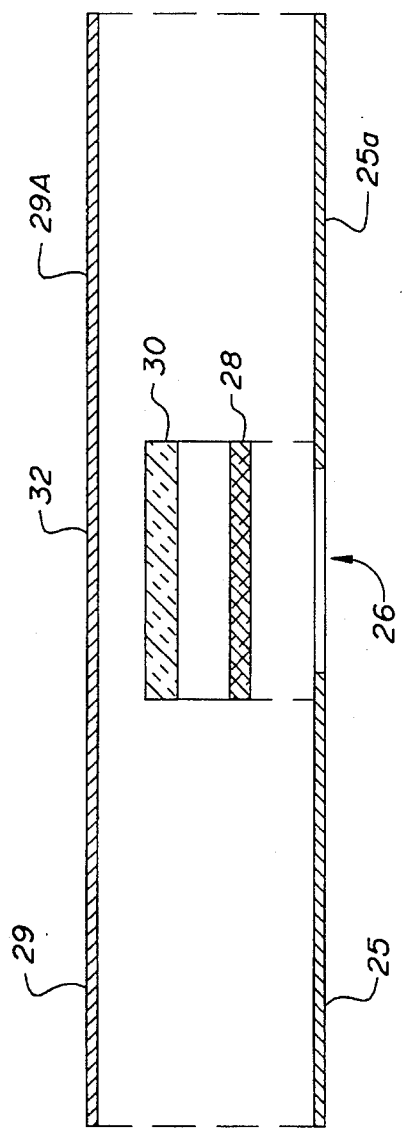
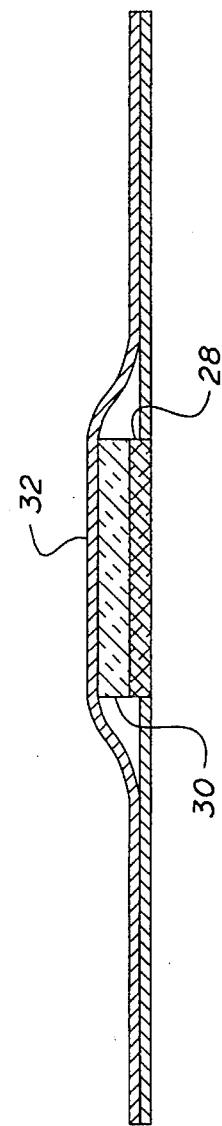
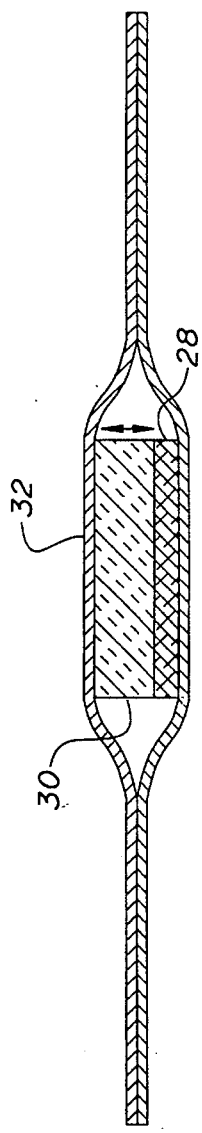
FIG. 3A
FIG. 3B
FIG. 3C

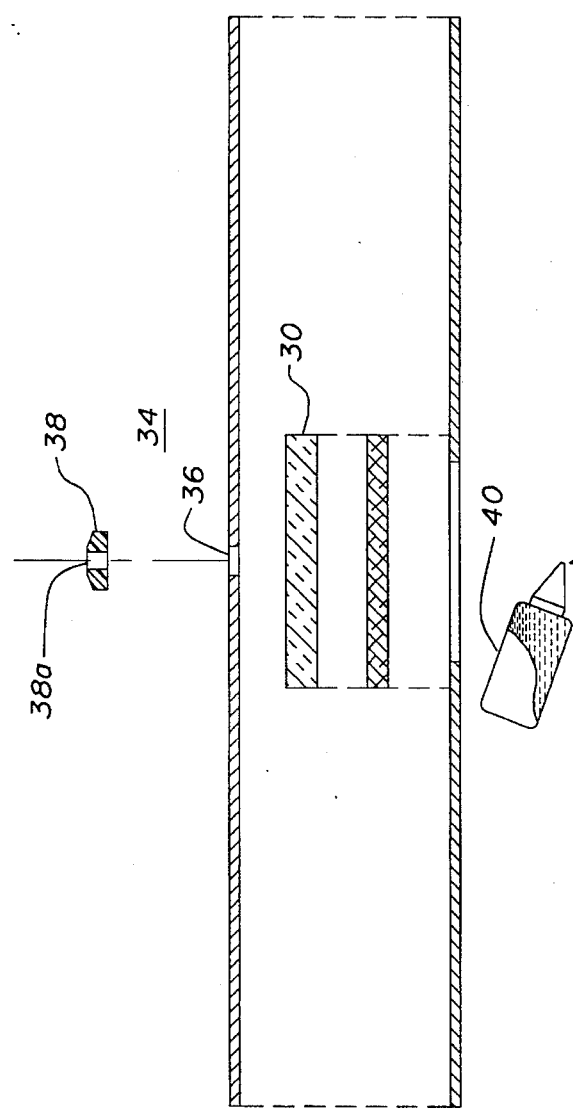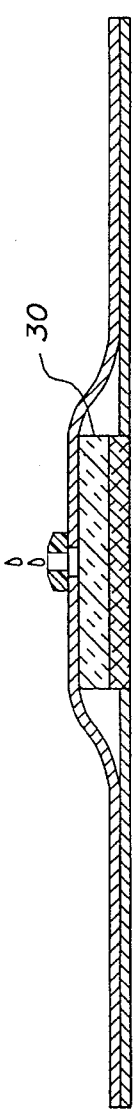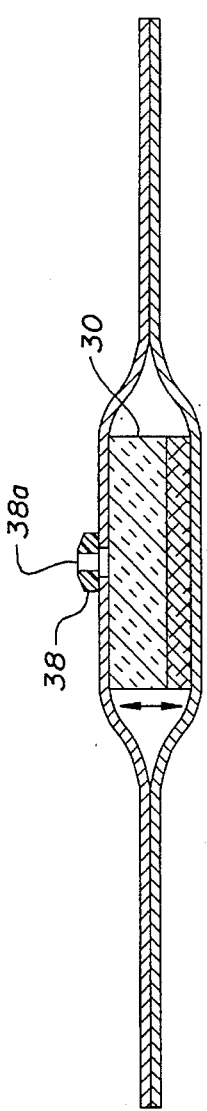
FIG. 4A
FIG. 4B
FIG. 4C

PROCESS FOR TREATING COMPRESSED CELLULOSE AND APPLICATIONS THEREOF

FIELD OF THE INVENTION

The present invention is directed to medical and dental sponges and absorbents, and specifically to the use of compressed cellulose as a sponge or absorbent for dental and/or medical use.

BACKGROUND OF THE INVENTION

There is an ongoing need for improved sponge-like and absorbent materials which may be utilized in dental and medical applications. To date, there have been a number of prior art patents in which an absorbent or sponge-like material is attached to a dental or medical implement.

U.S. Pat. No. 4,608,968 entitled "Gum Massaging Device with Internal Dispenser" discloses a gum massaging device within an internal dispenser. This patent discloses a toothbrush assembly having a handle, a brush assembly releasably interconnected with a second end of the handle and a massaging device. The massaging device includes a carrier which houses a container of liquid, positioned in an internal cavity of the carrier. The container is positioned so as to be broken and to dispense its contents when an end of a toothbrush is inserted into the carrier. A porous absorbent material forms an outer surface of the device and absorbs the liquid for application to the gums of the user.

Related U.S. Pat. No. 4,486,109 entitled "Toothbrush Assembly Combining Replaceable Brush Assembly with Massaging Device" also discloses a toothbrush having a porous absorbent material which forms an outer surface of the device and which absorbs a liquid for application to the gums of the user.

Finally, U.S. Pat. No. 4,543,679 entitled "Toothbrush Assembly Combining a Handle With A Replaceable Brush Assembly and a Replaceable Oral Hygiene Device" discloses a toothbrush which includes a removable oral hygiene device. The oral hygiene device can be used to apply a hygienic agent or as a oral stimulator. In a preferred embodiment, the hygienic device comprises compressed cellulose.

There have been a number of materials used to make absorbent pads and sponges for dental and medical applications. Compressed cellulose is an excellent material from which to make an absorbent pad or sponge. Cellulose is highly absorbent and can be compressed using simple compression techniques.

Unfortunately, compressed cellulose, as it comes manufactured and as it is shown, for example, in U.S. Pat. No. 4,543,679, is unacceptable for either dental or medical use, and cannot be approved for use by the U.S. Food and Drug Administration (F.D.A.). The undesirable side effects of untreated cellulose include unacceptable levels of organic residue; an unpleasant bitter taste; an ammonia odor which develops after use; the emission of a strong chemical smell; the creation of a burning sensation of the oral mucosa; the presence of trace amounts of a potential carcinogen, ethylurethane; the inconsistent ability of adhesives to bond the compressed cellulose to PVC and other materials; and inconsistencies between samples of cellulose resulting from the uncontrolled levels of chemicals. Heretofore, there has been no satisfactory method for cleaning cellulose for approval in medical and dental applications.

It would be desirable to provide a novel method for cleaning and purifying compressed cellulose so that it could be approved for use in dental and medical applications. Such a method could be utilized to enable the compressed cellulose to be used as a medical or dental sponge, absorbent, or applicator. Such a method could further be used to enable the compressed cellulose to be used as a compression bandage to actively apply pressure to a bleeding wound. By adding an access opening to such compressed cellulose bandage through the outer layer of the bandage, the compression bandage could be used as a transdermal patch enabling liquids or liquid/dry combinations to be systematically delivered to a wound or to the surface of the skin.

The present invention fulfills the desires and objectives set forth above, and the advantages of the present invention will become apparent from the following summary and detailed description which follow.

SUMMARY OF THE INVENTION

In accordance with the present invention, a method for removing extractables and chemicals from untreated cellulose is disclosed. The method comprises the following steps: immersing cellulose material in at least one acid bath so as to remove traces of organic extractables; immersing the cellulose material in water after said at least one acid bath; immersing the cellulose material in an alkaline bath; and sterilizing the cellulose material using at least one cycle of pressurized steam. The claimed method removes the extractables from the cellulose, thereby rendering it safe for medical/dental use and for meeting the requirements and standards of the F.D.A.

In yet a further embodiment, the present invention comprises a method for cleaning cellulose comprising the following steps: (a) immersing a cellulose material in one or more acid baths wherein said acid bath comprises a generally regarded as safe and effective (GRASE) acid; (b) immersing the cellulose material in water following each acid bath; (c) immersing the cellulose material in an alkaline bath comprising sodium bicarbonate; and (d) subjecting the cellulose material to pressurized steam.

In still a further embodiment, the compressed cellulose of the present invention is utilized in a novel compression bandage or transdermal patch bandage, capable of delivering liquids to the skin or to wounds. In the bandage embodiment, the novel bandage comprises: (a) a sanitary layer to be applied against the wound of a wearer; (b) a compressed cellulose interior layer; and (c) and an outer adhesive layer overlying said sanitary and compressed cellulose layers for applying the bandage to said wound, such that when blood or other bodily fluids are placed into contact with said compressed cellulose material layer, said layer expands against the sanitary and outer layers, and thereby applies pressure to the wound.

As a transdermal patch, the present invention comprises: a bandage comprising: (a) a bandage comprising:(i) a sanitary gauze layer to be applied against the skin; (ii) a compressed cellulose interior layer overlying said sanitary gauze layer; and (iii) an outside adhesive layer overlying said sanitary gauze and compressed cellulose layers and having adhesive wings which apply the bandage to a wound, said outer adhesive layer having an access hole in the region of said outer layer which overlies said compressed cellulose layer, whereby a liquid may be inserted into the compressed cellulose material and thereby expanding said cellulose layer and applying medication to the skin.

In yet a further embodiment, the present invention comprises a pressure bandage kit comprising: (a) a bandage comprising (i) a sanitary gauze layer to be applied against the wound of a wearer; (ii) a compressed cellulose interior layer; and (iii) and an outer adhesive layer overlying said sanitary gauge and compressed cellulose interior layer for applying the bandage to said wound, said outer adhesive layer having an aperture in a region of said outer layer overlying said compressed cellulose material layer whereby a liquid inserted into the compressed cellulose material layer thereby expanding the compressed cellulose of said layer and thereby applying pressure to the wound; and (b) a bottle containing a liquid to be inserted through said aperture to expand said compressed cellulose.

The compressed cellulose cleaned in accordance with the method of the present invention has a number of additional uses including as a pad for skin and nail care, a disposable diaper, and feminine hygiene sanitary napkin. The cleaned compressed cellulose of the present invention can also be used as a wet pack for treatment of insect bites, poison ivy, and rashes. Further the compressed cellulose cleaned in accordance with the present invention is suited for treatment of bed sores and for burns. As with such devices, all components of the device would be safe and effective and could be approved by the F.D.A.

BRIEF DESCRIPTION OF THE FIGURES

FIG. 3A is an exploded side perspective view of a pressure bandage having a compressed cellulose layer cleaned in accordance with the method of the present invention.

FIGS. 3B and 3C are side perspective views of the pressure bandage of the present invention before and after activation.

FIG. 4A is an exploded side perspective view of a transdermal patch having a compressed cellulose layer cleaned in accordance with the method of the present invention.

FIGS. 4B and 4C are side perspective views of the transdermal patch of the present invention before and after activation.

DETAILED DESCRIPTION OF THE PREFERRED EMBODIMENT

The present invention is described with reference to the enclosed Figures wherein the same numbers are utilized where applicable. In a broadest embodiment, the present invention is directed to a novel process for removing impurities from compressed cellulose and for applications of the compressed cellulose made using the process. The method of the present invention removes all undesirable chemicals and potential toxic substance from the cellulose.

Figure 1:
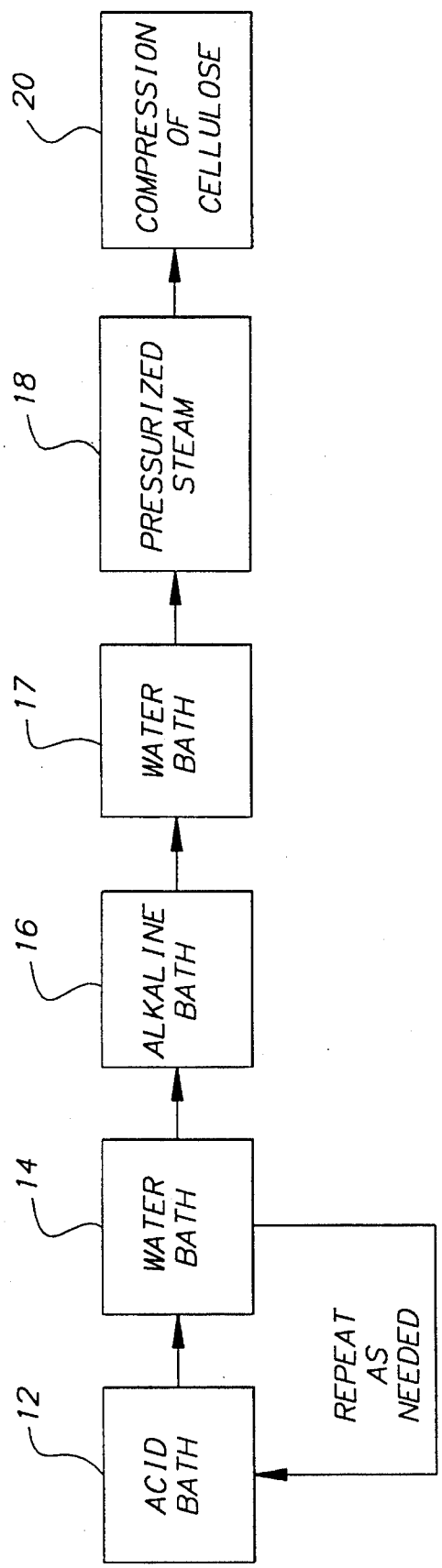
FIG. 1 is a block flow diagram of the method of the present invention.

Referring to FIG. 1, the cellulose sponge is washed in an acid bath 12 one or more times as required. The acid baths functions to remove all traces of chemicals and organic extractables from the cellulose. The acid used in the bath may comprise any acid, but should preferably be a GRASE acid (generally regarded as safe and effective), such as those approved for use by the U.S. Food and Drug Administration. The acid must also have as low a pK as possible.

The acid should preferably comprise one of the Krebs cycle acid metabolites because these acids are naturally occurring human metabolites that are approved by the Food and Drug Administration. The following acids exemplify the types of acids which may be used in the present invention: citric acid; acetic acid; isocitric acid; lactic acid; malic acid; oxalic acid; hydrochloric acid; fumaric acid; phosphoric acid; succinic acid; and tartaric acid. The optimum treatment time during which the cellulose should be placed in the acid bath is between 30 minutes and 20 hours.

After each immersion of the cellulose in the acid bath 12, the cellulose is immersed in a water bath 14 and both steps are repeated as needed. After the last washing cycle of acid 12 and water 14, the cellulose sponge is then immersed in an alkaline bath 16. Sodium bicarbonate is a preferred alkaline to be used in the method of the present invention, but any alkaline can be substituted for sodium bicarbonate, provided that it is safe for human use. The alkaline bath 16 neutralizes the pH of the cellulose, prevents the breakdown of the cellulose due to excess acid, functions as a preservative, and permits adhesive to bond properly in an alkaline environment.

The cellulose is then immersed in a second water bath 17. After water bath 17, the cellulose is then sterilized using one or more cycles of pressurized steam 18. This step not only cleans and sterilizes the sponge, but removes any remaining residue and eliminates any after taste. Finally, the cellulose is compressed using conventional mechanical pressure compression techniques 20 well known to those skilled in the art. The treated cellulose can then cut or formed into the appropriate shape. All of the above steps should be carried out in a clean room to maintain sterility.

The following example sets forth extraction studies conducted on samples of untreated cellulose containing ethyl carbonate. This study confirms that a 20 hour treatment of the untreated cellulose with a 0.1% solution of citric acid in water under ambient conditions, removed all extractables and yielded a clean sponge. Treatment times of between 5 minutes and 30 minutes failed to remove all the extractables from the sponge, indicating that the optimum treatment time is between 30 minutes and 20 hours.

EXAMPLE 1

Test Method 5.0 grams of a cellulose sample were cut into ½"×½" pieces and placed in a glass beaker containing 300 ml of 0.1% solution of citric acid in water at an ambient temperature of (26° C.). After the treatment, the sponge pieces were removed and the solution transferred to a separator funnel. Next, 200 ml of chloroform was added to the separator funnel and agitated for 1 minute. The chloroform was then drained from the funnel, another 200 ml of chloroform added and the procedure repeated. A total of 600 ml of chloroform was thus collected, reduced to approximately 10 ml using rotary evaporator, filtered and a 0.5 µl aliquot injected into a Gas Chromatograph.

| Test Results | |
|---|---|
| Sample | Results |
| 1. Spontex buff, untreated. 5 min. in 0.1% Citric Acid. | No detectable Ethyl Carbamate. Low level responses at 4.67 & 5.46 minutes. |
| 2. Sample #1 after a further 72 hours in 0.1% in 0.1% Citric acid. | No detectable Ethyl Carbamate. Low level responses at 5.79 & 7.44 minutes. |
| 3. Spontex buff, untreated. 30 min. in 0.1% Citric acid. | No detectable Ethyl Carbamate. Moderate response at 0.95 min. Low level responses at 2.87, 4.71, 4.95, 5.42 & 11.22 minutes. |
| 4. Sample #3 after a further 72 hours in 0.1% Citric acid. | No detectable Ethyl Carbamate. Low level responses at 4.57, 5.71 & 7.36. |
| 5. Spontex buff, untreated. 20 hours in 0.1% Citric Acid. | No detectable Ethyl Carbamate. Low level responses at 4.88, 5.38 & 10.44 minutes. |
| 6. Sample #5 after a further 72 hours in 0.1% Citric acid. | No detectable Ethyl Carbamate. Clean, no responses besides Chloroform. |

Gas Chromatograph
Manufacturer: Varian
Column: DB-17
Column Temperature: 60° C. for 2 min., 3° C. per min. to 80° C., 1 min. at 80° C.
Detector Temperature: 280° C.
Injector Temperature: 210° C.
Ethyl Carbamate retention time: 1.60 min.
The Ethyl Carbamate detection limit: 16 ng.

The cellulose cleaned in accordance with the method of the present invention may be utilized for a number of dental and medical applications, including use in a dental applicator, as well as in a novel compression pressure bandage and as a transdermal patch.

Figure 2:
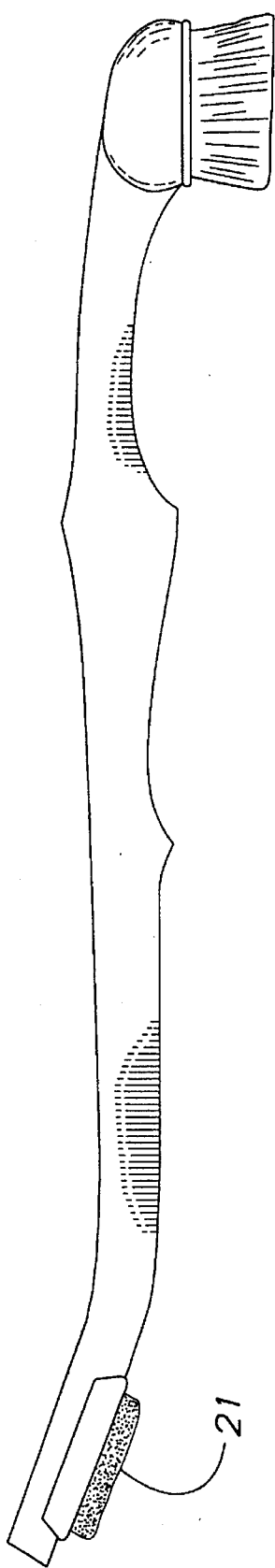
FIG. 2 is perspective views of a dental implement containing a massaging applicator constructed from cellulose cleaned in accordance with the present invention.
Figure 3:
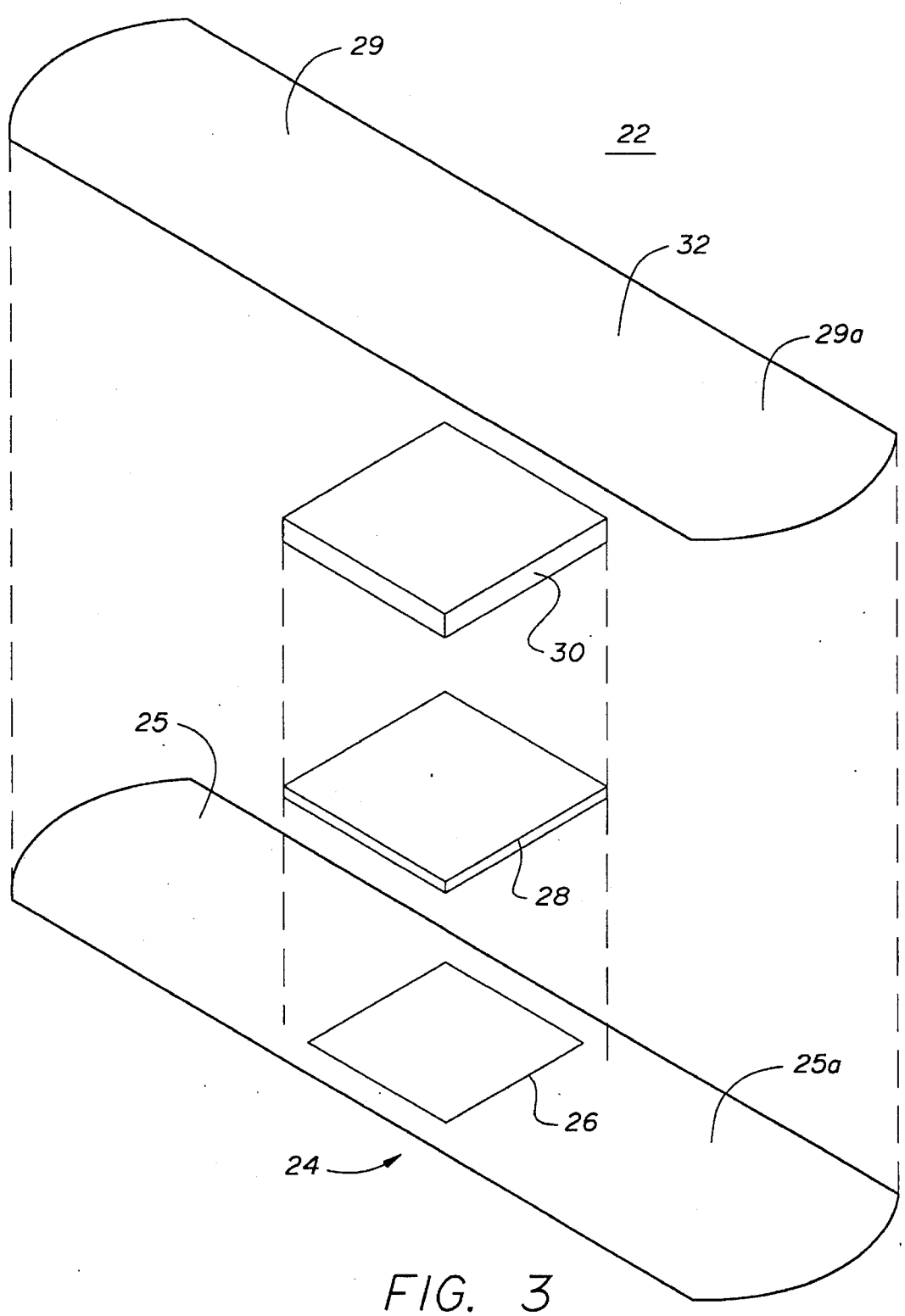
FIG. 3 is an exploded elevated view of a pressure bandage having a compressed cellulose layer cleaned in accordance with the method of the present invention.
Figure 4:
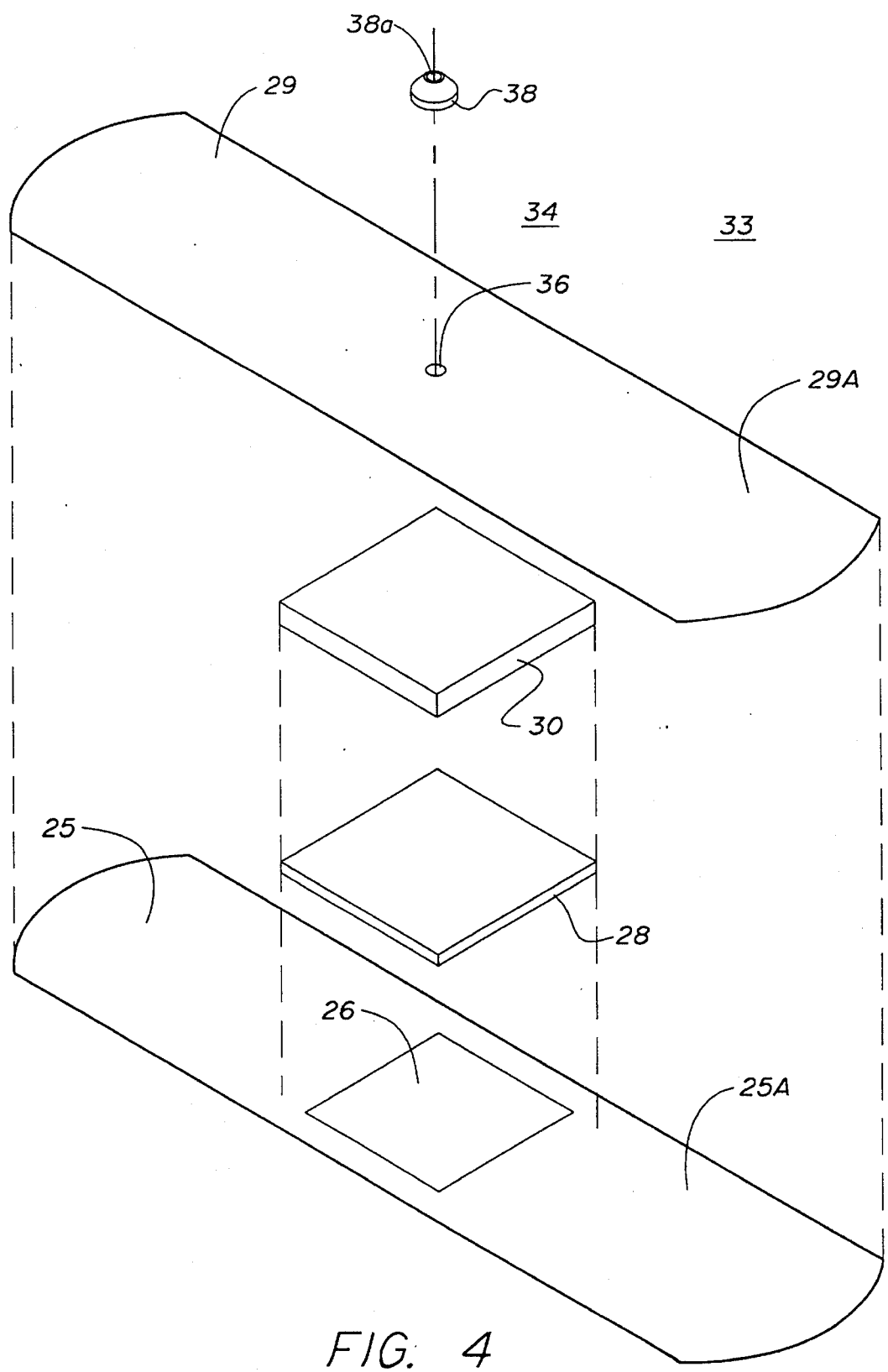
FIG. 4 is an exploded elevated view of a transdermal patch having a compressed cellulose layer cleaned in accordance with the method of the present invention.
Figure 5:
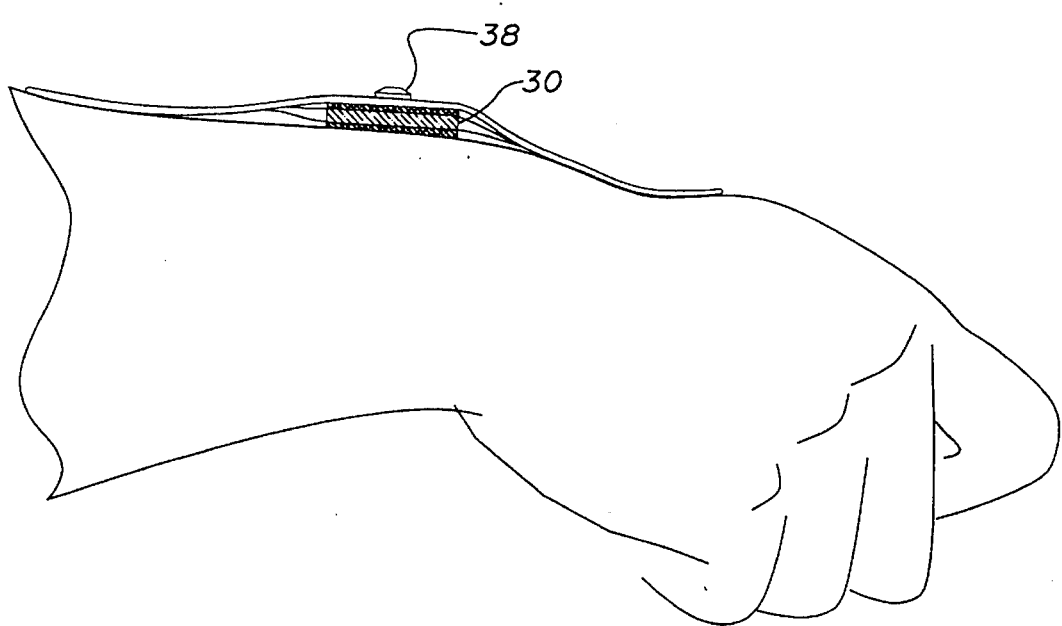
FIGS. 5 and 5A are side perspective views of the transdermal patch of the present invention applied to a human hand both before and after activation.
Figure 5A:
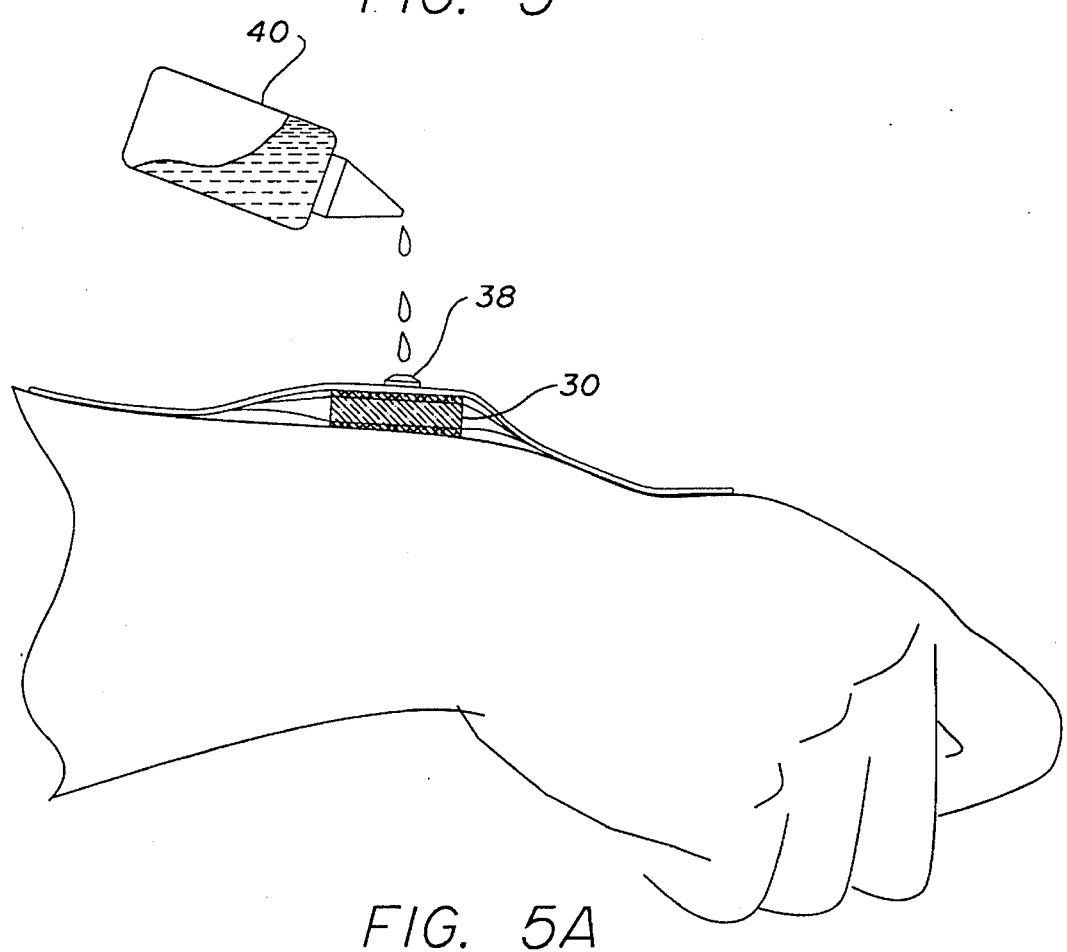

Initially, the compressed cellulose cleaned in accordance with the present invention may be utilized as an absorbent attachment for a toothbrush to be used to massage teeth and gums. Such an application is shown as material 66' in U.S. Pat. No. 4,608,968 and massaging device 26 in U.S. Pat. No. 4,486,109. The tooth brush of FIG. 2 herein includes a massage applicator 21 made of compressed cellulose, cleaned in accordance with the method of the present invention.

In additional applications, the compressed cellulose cleaned in accordance with the method of the present invention can be used to construct a pressure bandage and a transdermal patch bandage. Referring to FIGS. 3, 3A, 3B and 3C, the compression bandage 22 of the present invention is used to put active pressure on a bleeding wound. The theory of operation of the compression bandage 22 is based upon the tendency of compressed cellulose to absorb liquids and to rapidly expand.

Referring to FIGS. 3, 3A–3C, the compression bandage 22 of the present invention is multi-layered. A packet or envelope is formed that may be heat sealed for closure. The side 24 that is placed against the skin has a window 26 cut into it. The side may have adhesive wings 25, 25a which attach to the skin. The window is covered by a layer of a porous absorbent sterile non stick pad 28. Pad 28 comprises a sanitary layer of a material such as a gauze, which is placed directly against the bleeding wound. A second or interior layer 30 comprises a compressed cellulose pad cleaned in accordance with the method of the present invention. The compressed cellulose can optionally be impregnated with a dry medication such as a hemostatic powder or an antiseptic powder or other dry ingredients. The next layer 32 is an adhesive layer overlaying the sanitary layer 28 and compressed cellulose layer 30 for applying the bandage to the wound. Layer 32 comprises a polymeric or woven adhesive placed over layers 28 and 30, and includes adhesive wings 29, 29a which attach the over wings 25, 25a. A release liner (not shown) prevents the adhesive layer from sticking until ready for use.

The compression bandage 22 is activated by the victim's blood that flows through the gauze layer to the cellulose layer 30. The compressed cellulose soaks up the blood and blooms or expands as shown in FIGS. 3B and 3C. The compressed cellulose swells and compresses against the walls of the packet, putting active pressure to the bleeding wound. If medication is impregnated in the compressed cellulose the natural moisture at the wound site will release the medication. The compression bandage will help to stop the bleeding and will create a tight seal to prevent dirt and other contaminants from reaching the wound. The bloomed compressed cellulose is soft and pliable and is an excellent protective layer preventing further trauma to the wound.

Referring to FIGS. 4, 4A–4C, 5 and 5A, a transdermal patch 33 utilizing the cleaned compressed cellulose of the present invention is shown. In a preferred embodiment, the layer structure of transdermal patch is identical that shown in FIGS. 3–3C. In this embodiment, a feed mechanism 34 is included. In a preferred embodiment, the feed mechanism 34 comprises an access hole 36 punched in the outer layer 32. A disk 38 having a central aperture 38a is adhered over the access hole 36. The disk 38 may be funnel shaped so as to prevent liquids from escaping. A measured dose of liquid may thereby be introduced via a squeeze bottle 40 into the access hole 36, through the feeder disk 38 directly to the compressed cellulose 30 as shown most particularly in FIGS. 5 and 5A. Once the compressed cellulose blooms or expands the hole in the feeder disk can be covered to maintain sterility. It is to be appreciated that the compression bandage and transdermal patch may come as part of a kit including squeeze bottle 40 containing a predetermined and premeasured quantity of liquid or medication.

Other possible uses for compressed cellulose cleaned in accordance with the present invention include use in skin and nail care, in disposable diapers, in feminine sanitary napkins, in wet packs for treatment of insect bites, poison ivy and burns. Bandages incorporating cellulose cleaned in accordance with the method of the present invention can also be used in treatment of bed sores. The common feature for all these medical/dental applications is the use of safe compressed cellulose which meets F.D.A. standards.

The present invention has been described with reference to the above-discussed preferred embodiments. It is to be appreciated that other embodiments will fulfill the spirit and scope of the present invention, and that the true nature of the present invention is to be determined with respect to the claims appended hereto.

What is claimed is:

1. A method for removing organic extractables from a compressible cellulose such that said cellulose may be used for medical/dental applications comprising the following steps:

(a) providing a cellulose material;
   (b) immersing the cellulose material containing organic extractables in one or more acid baths comprising a Krebs cycle acid metabolite so as to remove traces of said organic extractables;

(c) immersing the cellulose material in a water bath;

(d) immersing the cellulose material in an alkaline bath; and (e) treating the cellulose material using pressurized steam for a time sufficient to remove all traces of impurities, said method enabling said cellulose to be recompressed and safely used for dental and medical applications.

2. The method of claim 1 further comprising the step of physically compressing the cellulose material after treatment by pressurized steam.

3. The method of claim 1 wherein said alkaline comprises sodium bicarbonate.

4. The method of claim 1 wherein said acid is citric acid.

5. The method of claim 1 wherein said acid is acetic acid.

6. A method for cleaning cellulose such that said cellulose can be recompressed and used for medical or dental applications comprising the following steps:

(a) providing a cellulose material;

(b) immersing the cellulose material in one or more acid baths wherein said acid bath comprises a Krebs cycle acid metabolite;

(c) immersing the cellulose material in a water bath;

(d) immersing said cellulose material in an alkaline bath comprising sodium bicarbonate; and (e) subjecting the cellulose material to pressurized steam for a time sufficient to remove the organic extractables, said method enabling said cellulose to be recompressed for safe use in dental or medical applications.

7. The method of claim 6 further comprising the step of physically compressing the cellulose material.

* * * * *